United States Patent
Johnson

(10) Patent No.: US 10,233,427 B2
(45) Date of Patent: *Mar. 19, 2019

(54) FIBER SCAFFOLDS FOR USE IN ESOPHAGEAL PROSTHESES

(71) Applicant: NANOFIBER SOLUTIONS, INC., Hilliard, OH (US)

(72) Inventor: Jed Johnson, London, OH (US)

(73) Assignee: NANOFIBER SOLUTIONS, LLC, Hilliard, OH (US)

( * ) Notice: Subject to any disclaimer, the term of this patent is extended or adjusted under 35 U.S.C. 154(b) by 91 days.

This patent is subject to a terminal disclaimer.

(21) Appl. No.: 14/940,363

(22) Filed: Nov. 13, 2015

(65) Prior Publication Data

US 2016/0325019 A1 Nov. 10, 2016

Related U.S. Application Data

(63) Continuation of application No. 13/385,612, filed on Feb. 9, 2012.

(60) Provisional application No. 61/466,039, filed on Mar. 22, 2011, provisional application No. 61/562,090, filed on Nov. 21, 2011, provisional application No. 61/585,869, filed on Jan. 12, 2012.

(51) Int. Cl.

| | |
|---|---|
| *C12N 5/071* | (2010.01) |
| *A61L 27/38* | (2006.01) |
| *C12N 5/00* | (2006.01) |
| *A61L 27/14* | (2006.01) |
| *A61L 27/36* | (2006.01) |
| *A61L 27/50* | (2006.01) |
| *A61L 27/18* | (2006.01) |

(52) U.S. Cl.
CPC ............ *C12N 5/0697* (2013.01); *A61L 27/14* (2013.01); *A61L 27/18* (2013.01); *A61L 27/3612* (2013.01); *A61L 27/3679* (2013.01); *A61L 27/3691* (2013.01); *A61L 27/38* (2013.01); *A61L 27/3882* (2013.01); *A61L 27/507* (2013.01); *C12N 5/0068* (2013.01); *A61L 2430/22* (2013.01); *C12N 2533/30* (2013.01)

(58) Field of Classification Search
CPC ............... A61L 2430/02; A61L 27/507; A61L 2400/12; A61L 2430/22; A61L 31/18; D01D 5/0038; C08L 23/06; D01F 6/70; D01F 6/62; D04H 1/728; B32B 2262/0292; C12N 5/0068; C12N 2533/30; C12N 2513/00; A61F 2/06; A61K 9/0092; D10B 2331/10; B01D 2323/39; B01J 35/1061; C12M 25/14
See application file for complete search history.

(56) References Cited

U.S. PATENT DOCUMENTS

| | | | |
|---|---|---|---|
| 4,693,721 A | 9/1987 | Ducheyne | |
| 4,738,740 A | 4/1988 | Pinchuk et al. | |
| 5,258,027 A | 11/1993 | Berghaus | |
| 5,628,788 A | 5/1997 | Pinchuk | |
| 6,143,022 A | 11/2000 | Shull et al. | |
| 6,635,082 B1* | 10/2003 | Hossainy | A61F 2/91 623/1.15 |
| 7,115,220 B2 | 10/2006 | Dubson et al. | |
| 7,172,765 B2 | 2/2007 | Chu et al. | |
| 7,220,281 B2 | 5/2007 | Lambrecht et al. | |
| 7,390,760 B1 | 6/2008 | Chen et al. | |
| 7,490,563 B2 | 2/2009 | Eastin et al. | |
| 7,629,030 B2 | 12/2009 | Robertson et al. | |
| 7,718,351 B2 | 5/2010 | Ying et al. | |
| 7,993,567 B2 | 8/2011 | Scott-Carnell et al. | |
| 8,157,722 B2 | 4/2012 | Arnal et al. | |
| 8,623,085 B2 | 1/2014 | Gatt et al. | |
| 8,821,441 B2 | 9/2014 | Wilson et al. | |
| 2002/0090725 A1 | 7/2002 | Simpson et al. | |
| 2002/0142458 A1 | 10/2002 | Williams et al. | |
| 2003/0168756 A1 | 9/2003 | Balkus, Jr. et al. | |
| 2003/0226750 A1 | 12/2003 | Fenn | |
| 2005/0177249 A1 | 8/2005 | Kladakis et al. | |
| 2005/0277985 A1 | 12/2005 | Wert et al. | |
| 2006/0060999 A1 | 3/2006 | Amagasa et al. | |
| 2006/0085063 A1* | 4/2006 | Shastri | A61F 2/02 623/1.41 |
| 2006/0134157 A1 | 6/2006 | Lehman et al. | |
| 2006/0135020 A1 | 6/2006 | Weinberg et al. | |
| 2006/0154063 A1 | 7/2006 | Fujihara et al. | |
| 2006/0200232 A1 | 9/2006 | Phaneuf et al. | |

(Continued)

FOREIGN PATENT DOCUMENTS

| | | |
|---|---|---|
| CN | 102008755 A | 4/2011 |
| EP | 0416846 A2 | 3/1991 |

(Continued)

OTHER PUBLICATIONS

Ayres et al. Microvascular endothelial cell migration in scaffolds of electrospun collagen. Wound Repair and Regeneration. 2005;13(2):A6.*

(Continued)

*Primary Examiner* — Lynn Y Fan

(74) *Attorney, Agent, or Firm* — Pepper Hamilton LLP

(57) ABSTRACT

The development and construction of implantable artificial organs, and a process for manufacturing three-dimensional polymer microscale and nanoscale structures for use as scaffolds in the growth of biological structures such as hollow organs, luminal structures, or other structures within the body are disclosed.

13 Claims, 7 Drawing Sheets

(5 of 7 Drawing Sheet(s) Filed in Color)

(56) References Cited

U.S. PATENT DOCUMENTS

| | | |
|---|---|---|
| 2006/0204539 A1 | 9/2006 | Atala et al. |
| 2007/0142907 A1 | 6/2007 | Moaddeb et al. |
| 2007/0191956 A1 | 8/2007 | Prewett et al. |
| 2007/0232169 A1 | 10/2007 | Stricklet et al. |
| 2007/0269481 A1 | 11/2007 | Li et al. |
| 2007/0286880 A1 | 12/2007 | Vasiliev et al. |
| 2008/0208323 A1 | 8/2008 | El-Kurdi et al. |
| 2008/0208358 A1 | 8/2008 | Bellamkonda et al. |
| 2009/0018643 A1 | 1/2009 | Hashi et al. |
| 2009/0108503 A1 | 4/2009 | Scott-Carnell et al. |
| 2009/0143855 A1 | 6/2009 | Weber et al. |
| 2009/0152773 A1 | 6/2009 | Barinov et al. |
| 2009/0162468 A1 | 6/2009 | Barinov et al. |
| 2009/0253328 A1 | 10/2009 | Watanabe et al. |
| 2010/0041292 A1 | 2/2010 | Kim et al. |
| 2010/0082114 A1 | 4/2010 | Gingras et al. |
| 2010/0105799 A1 | 4/2010 | Rudd et al. |
| 2010/0166854 A1 | 7/2010 | Michniak-Kohn et al. |
| 2010/0222771 A1 | 9/2010 | Mitchell et al. |
| 2010/0233115 A1 | 9/2010 | Patel et al. |
| 2010/0273258 A1 | 10/2010 | Lannutti et al. |
| 2010/0303881 A1 | 12/2010 | Hoke et al. |
| 2011/0022149 A1 | 1/2011 | Cox et al. |
| 2011/0028834 A1 | 2/2011 | Zussman |
| 2011/0030885 A1 | 2/2011 | Anneaux et al. |
| 2011/0070283 A1 | 3/2011 | Hossainy et al. |
| 2011/0083987 A1 | 4/2011 | Rolland et al. |
| 2011/0098826 A1 | 4/2011 | Mauck et al. |
| 2011/0166647 A1 | 7/2011 | Hashi et al. |
| 2011/0177395 A1 | 7/2011 | Kamisasa |
| 2011/0270412 A1 | 11/2011 | Bellan et al. |
| 2012/0068384 A1 | 3/2012 | Phaneuf et al. |
| 2012/0093717 A1 | 4/2012 | Mauck et al. |
| 2012/0271405 A1 | 10/2012 | Soletti |
| 2013/0150963 A1 | 1/2013 | Johnson |
| 2013/0066438 A1 | 3/2013 | Seifalian |
| 2013/0103079 A1 | 4/2013 | Lau et al. |
| 2013/0310920 A1 | 11/2013 | Su |
| 2014/0030315 A1 | 1/2014 | Johnson |
| 2014/0057346 A1 | 2/2014 | Johnson |
| 2014/0272225 A1 | 9/2014 | Johnson |
| 2014/0309726 A1 | 10/2014 | Wang |
| 2014/0332733 A1 | 11/2014 | Joo et al. |
| 2015/0132423 A1 | 5/2015 | Johnson |
| 2017/0119886 A1 | 5/2017 | Johnson et al. |
| 2017/0182206 A1 | 6/2017 | Johnson et al. |

FOREIGN PATENT DOCUMENTS

| | | |
|---|---|---|
| EP | 242203 A | 10/2010 |
| WO | 1991018612 A1 | 12/1991 |
| WO | WO 2000/010622 A1 | 3/2000 |
| WO | WO2001/015754 A1 | 3/2001 |
| WO | WO2005/012606 A2 | 2/2005 |
| WO | WO 2005/096989 A1 | 10/2005 |
| WO | WO2006/138552 A2 | 12/2006 |
| WO | WO2008/137659 A1 | 11/2008 |
| WO | WO2009/089035 A1 | 7/2009 |
| WO | WO 2010/040129 A3 | 4/2010 |
| WO | WO 2010/048281 A1 | 4/2010 |
| WO | WO2010/124207 A1 | 10/2010 |
| WO | WO2013/078051 A1 | 5/2013 |
| WO | WO2013/106822 A1 | 7/2013 |
| WO | WO2014/031721 A1 | 2/2014 |
| WO | WO2014/145864 A1 | 9/2014 |
| WO | WO 2015/153011 A1 | 10/2015 |
| WO | 2017079328 A1 | 5/2017 |

OTHER PUBLICATIONS

Aboitiz et al., "Fiber composition of the human corpus callosum", Brain Res. 598(1-2):143-153, (Dec. 11, 1992), (Abstract only).

Alexis et al., "In Vivo Particle Uptake by Airway Macrophages in Healthy Volunteers" Am. J. Respir Cell Mol. Biol. 34(3): 305-313, (2006).

Band et al., "Antiproliferative effect of gossypol and its optical isomers on human reproductive cancer cell lines", Gynecologic Oncology 32(3):273-277, (1989), (Abstract only).

Bandtlow et al., "Proteoglycans in the developing brain: new conceptual insights for old proteins" Physiol. Rev. 80(4): 1267-1290, (2000).

Baran et al., "Important roles for macrophage colony-stimulating factor, CC chemokine ligand 2, and mononuclear phagocytes in the pathogenesis of pulmonary fibrosis" Am. J. Respir. Crit. Care Med., 176(1):78-89, (2007).

Bellail et al., "Microregional extracellular matrix heterogeneity in brain modulates glioma cell invasion", Int. J. Biochem. Cell Biol. 36(6):1046-1069 (2004), (Abstract only).

Beningo et al., "Nascent Focal Adhesions Are Responsible for the Generation of Strong Propulsive Forces in Migrating Fibroblasts", J. Cell Biol., 153(4):881-887, (May 14, 2001).

Benz et al., "Biochemical Correlates of the Antitumor and Antimitochondrial Properties of Gossypol Enantiomers", Mol. Pharma. 37(6):840-847, (1990), (Abstract only).

Benz et al., "Lactic Dehydrogenase Isozymes, P Magnetic-Resonance Spectroscopy, and In Vitro Antimitochondrial Tumor Toxicity With Gossypol and Rhodamine-123", J. Clin. Invest. 79(2):517-523, (1987).

Benz et al., "Selective toxicity of gossypol against epithelial tumors and its detection by magnetic resonance spectroscopy",Contraception 37(3):221-228, (1998), (Abstract only).

Bernstein et al., "Glioblastoma cells do not intravasate into blood vessels", Neurosurgery 36(1):124-132, (1995), (Abstract only).

Bershadsky et al., "Adhesion-mediated mechanosensitivity: a time to experiment, and a time to theorize", Curr. Opn. Cell Biol. 18(5):472-481, (2006), (Abstract only).

Binder et al., "Proteases and the Biology of Glioma Invasion", J. Neuro-Oncology, 56:149-158, (2002).

Bucala et al., "Circulating Fibrocytes Define a New Leukocyte Subpopulation That Mediates Tissue Repair", Mol. Med. 1(1):71-81, (1994), (Abstract only).

Camoretti-Mercado "Targeting the airway smooth muscle for asthma treatment", Translational Research 154(4):165-174, (2009), (Abstract only).

Cattaruzza et al., "Proteoglycan control of cell movement during wound healing and cancer spreading", Matrix Biol. 24(6):400-417, (2005), (Abstract only).

Central Brain Tumor Registry of the United States, Primary Brain Tumors in the United States—Statistical Report 1998-2002, CBTRUS, 2005-2006.

Chicoine et al., "Assessment of brain-tumor cell motility in vivo and in vitro", J. Neurosurg. 82(4):615-622, (1995), (Abstract only).

Chew et al., "The Role of Electrospinning in the Emerging Field of Nanomedicine" Curr. Pharm. Sec. 12(36)A:4751-4770, (2006).

Choi et al., "Structuring electrospun polycaprolactone nanofiber tissue scaffolds by femtosecond laser ablation", J. Laser Appl., 19(4):225-231, (2007).

Cukierman et al., "Taking cell-matrix adhesions to the third dimension", Science, 294:1708-1712, (Nov. 23, 2001).

Davis et al. "Injectable biomaterials for the treatment of stress urinary incontinence: their potential and pitfalls as urethral bulking agents", Int Urogynecol J. 24:913-919 (2013).

Davies et al. "Adult axon regeneration in adult CNS white matter", Trends Neurosci. 21(12):515ABS, (Dec. 1, 1998).

Diaz et al., "Controlled encapsulation oh hydrophobic liquids in hydrophilic polymer nanofibers by co-electrospinning", Adv. Funct. Mater., 16(16):2110-2116, (2006).

Discher et al., "Tissue cells feel and respond to the stiffness of their substrate", Science, 310:1139-1143, (Nov. 18, 2005).

Drilling et al. "Fabrication of burst pressure competent vascular grafts via electrospinning: Effects of microstructure", J. Miomed. Mat. Res. Part A 88A(4):923-934, (Mar. 15, 2009), (Abstract only).

Duling et al. "Mechanical characterization of electrospun Polycaprolactone (PCL): a potential scaffold for tissue engineering", J. Biomech. Eng. 130(1) No. 011006, (2008), (Abstract only).

(56) References Cited

OTHER PUBLICATIONS

Engler et al., "Matrix Elasticity Directs Stem Cell Lineage Specification", *Cell*, 126(4):677-689, (Aug. 25, 2006).
Epperly et al., "Correlation of Ionizing Irradiation-induced Late Pulmonary Fibrosis with Long-term Bone Marrow Culture Fibroblast Progenitor Cell Biology in Mice Homozygous Deletion Recombinant Negative for Endothelial Cell Adhesion Molecules", *In Vivo*, 18(1):1-14, (2004).
Farin et al., "Transplanted glioma cells migrate and proliferate on host brain vasculature: a dynamic analysis", *Glia* 53(8):799-808, (2006), (Abstract only).
Fathallah-Shaykh "Darts in the Dark Cure Animal, but Not Human, Brain Tumors", *Arch. Neurol.* 59:721-724, (2002), (Abstract only).
Fujihara et al., "Guided bone regeneration membrane made of Polycaprolactone/calcium carbonate composite nano-fibers", *Biomaterials* 26(19):4139-4147, (2005), (Abstract only).
Furnari et al., "Malignant astrocytic glioma: genetics, biology, and paths to treatment", *Genes Dev.*, 21:2683-2710, (2007).
Gaumer et al., "Structure-function relationships and Source-to-ground Distance and the Mechanical Properties of Electrospun Fiber" *Acta Biomaterialia* 5(5):1552-1561, (Jan. 31, 2009), (Abstract only).
Geiser et al., "The Role of Macrophages in the Clearance of Inhaled Ultrafine Titanium Dioxide Particles", *Am. J. Respir. Cell Mol. Biol.*, 38(3):371-376, (2008).
Georges et al., "Cell type-specific response to growth on soft materials", *J. Appl. Physiol*, 98:1547-1553, (2005).
Georges et al., "Matrices with compliance comparable to that of brain tissue select meuronal over glial growth in mixed cortical cultures," Biophys. J., 90:3012-3018, (2006).
Giese et al., "Dichotomy of astrocytoma migration and proliferation", *Int. J. Cancer*, 67:275-282, (1996).
Giese et al., "Migration of Human Glioma Cells on Myelin", *Neurosurgery* 38(4):755-764, (1996), (Abstract only).
Giese et al., "Substrates for astrocytoma invasion", *Neurosurgery* 37(2):294-302, (1995), (Abstract only).
Gilbert et al., "Antiproliferative activity of gossypol and gossypolone on human breast cancer cells", *Life Sciences* 57(1):61-67, (May 26, 1995), (Abstract only).
Gladson, "The Extracellular Matrix of Gliomas: Modulation of Cell Function", *J. Neuropath. Exper. Neur.* 58(10):1029-1040, (1999), (Abstract only).
Goldbrunner et al., "Cell-extracellular matrix interaction in glioma invasion", *Acta Neurochir (Wien)*, 141:295-305, (1999).
Grandpre et al., "Nogo: a molecular determinant of axonal growth and regeneration", *Neuroscientist* 7(5):377-386, (2001), (Abstract only).
Haley et al., "Study of myelin purity in relation to axonal contamination", *Cell Mol. Neurobiol.*, 1:175-187, (1980), (Abstract only).
Hashi et al., "Antithrombogenic property of bone marrow mesenchymal stem cells in nanofibrous vascular grafts", *PNAS* 104(29):11915-11920, (2007).
He et al., "Fabrication of Drug-Loaded Electrospun Aligned Fibrous Threads for Suture Applications", *J. Biomed. Mater. Research. Part A.*, 89(1):80-95, (2009).
Hinz et al., "Alpha-smooth muscle actin expression upregulates fibroblast contractile activity", *Molecular Biology of the Cell*, 12(9):2730-2741, (2001).
Holland, "Glioblastoma multiforme; the terminator", PNAS USA, 97(12):6242-6244, (Jun. 6, 2000).
Hsu et al., "N,N-Dimethylformamide Additions to the Solution for the Electrospinning of Poly(ε-caprolactone) Nanofibers", *Macromolecular Materials and Engineering* 289(4):334-340, (2004), (Abstract only).
Hsu et al., "Nano-sized beads and porous fiber constructs of Poly(ε-caprolactone) produced by electrospinning", *Journal of Material Science*, 39(9):3003-3013, (2004).
Hu et al., "Gossypol inhibits basal and estrogen-stimulated DNA synthesis in human breast carcinoma cells", *Life Sciences* 53(25):PL433-PL438, (1993), Abstract only.

Hu et al., "Regulating axon growth within the postnatal central nervous system", *Semin Perinatol*, 28(6):371-378, (2004).
Hu et al., "The proteoglycan brevican binds to fibronectin after proteolytic cleavage and promotes glioma cell motility", *Journal of Biological Chemistry*, 283(36):24848-24859, (Sep. 5, 2008).
Huang et al., "A review on polymer nanofibers by electrospinning and their applications in nanocomposites", *Composites Science and Technology*, 63(15):2223-2253, (2003), Abstract only.
International Search Report and Written Opinion for PCT/US2013/055941 dated Nov. 12, 2013.
International Search Report and Written Opinion for PCT/US2015/016973 dated May 22, 2015.
Jaroszewski et al., "Action of Gossypol and Rhodamine 123 on Wild Type and Multidrug-resistant MCF-7 Human Breast Cancer Cells: P Nuclear Magnetic Resonance and Toxicity Studies", *Cancer Research*, 50(21:6936-6943, (1990).
Johnson, "First-in-the-World Equine Joint Injection for Osteoarthritis", *The International Equine Veterinarian* , 23-25 (2014).
Johnson et al., "Microstructure-Property Relationships in a Tissue-Engineering Scaffold", *Journal of Applied Polymer Science* 104(5):2919-2927, (2007).
Johnson et al., "Quantitative Analysis of Complex Glioma Cell Migration on Electrospun Polycaprolcatone Using Time-Lapse Microscopy" *Tissue Engineering Part C* 15(4):531-540, (2009).
Johnson et al., "Electrospun PCL in Vitro: a Microstructural Basis for Mechanical Property Changes", *Journal of Biomaterials Science, Polymer Edition*, 20(4):467-481, (2009), Abstract only.
Jung et al., "Tracking the invasiveness of human astrocytoma cells by using green fluorescent protein in an organotypical brain slice model" , *J. Neurosurgery* 94(1):80-89, (2001), Abstract only.
Kang et al., "Plasma Treatment of Textiles—synthetic Polymer-Base Textiles", *AATCC Review*, 4(11):29-33, (2004).
Katta et al., "Continuous electrospinning of aligned polymer nanofibers onto a wire drum collector", *Nano Letters*, 4(11):2215-2218, (Sep. 28, 2004), (Abstract only).
Kazemnejad et al., "Biochemical and Molecular Characterization of Hepatocyte-Like Cells Derived from Human Bone Marrow Mesenchymal Stem Cells on a Novel Three-Dimensional Biocompatible Nanofibrous Scaffold", *J. Gastronenter. Hepatol*, 24(2):278-287, (Feb. 1, 2009).
Khil et al., "Novel fabricated matrix via electrospinning for tissue engineering", Journal of Biomedical Materials Research Part B—Applied Biomaterials 72B(1):117-124, (2005).
Kim et a., "Controlled protein release from electrospun biodegradable fiber mesh composed of poly(ε-caprolactone) and poly(ethylene oxide)", *International Journal of Pharmaceutics* 338 (1-2):276-283, (Jun. 29, 2007), (Abstract only).
Kim et al., "Epithelial cell α3β1 integrin links β-catenin and Smad signaling to promote myofibroblast formation and pulmonary fibrosis", *Journal of Clinical Investigation*, 119(1):213-224, (2009).
Kleihues et al., "The WHO Classification of Tumors of the Nervous System", *J. Neuropathol. Exp. Neurol*. 61(3):215-225, (2002), (Abstract only).
Klim et al., "A Defined Glycosaminoglycan-Binding Substratum for Human Pluripotent Stem Cells", *Nature Methods* 7(23):989-996, (2010), (Abstract only).
Ko et al., "High Percentage of False-Positive Results of Cytokeratin 19 RT-PCR in Blood: A Model for the Analysis of Illegitimate Gene Expression", *Oncology* 59:81-88, (2000), (Abstract only).
Kwon et al., "Electrospun nano- to microfiber fabrics made of biodegradable copolyesters: structural characteristics, mechanical properties and cell adhesion potentiar", *Biomaterials* 26(18):3929-3939, (2005), (Abstract only).
Lannutti et al., "Electrospinning for tissue engineering scaffolds", *Materials Science and Engineering: C* 27(3):504-509, (2007), (Abstract only).
Leblanc et al., "An in vitro study of inhibitory activity of gossypol, a cottonseed extract, in human carcinoma cell lines", *Pharmacological Research* 46(6):551-555, (2002), (Abstract only).
Lee et al., "Characterization of nano-structured poly(ε-caprolactone) nonwoven mats via electrospinning", *Polymer* 44(4):1287-1294, (2003), (Abstract only).

(56) References Cited

OTHER PUBLICATIONS

Lesma et al., "Glycosaminoglycans in nerve injury: I. Low doses glycosaminoglycans promote neurite formation", *J. Neurosci. Res.*, 46(5):565-571, (Dec. 1, 1996), (Abstract only).

Levicar et al., "Proteases in brain tumor progression", Acta Neurochir. (Wien.), 145:825-838, (2003).

Levina et al., "Chemotherapeutic drugs and human tumor cells cytokine network", *International Journal of Cancer*, 123(9):2031-2040, (2008).

Li et al., "A three-dimensional nanofibrous scaffold for cartilage tissue engineering using human mesenchymal stem cells", *Biomaterials*, 26(6):599-609, (2005), (Abstract only).

Li et al., "Biological response of chondrocytes cultured in three-dimensional nanofibrous poly(ε-caprolactone) scaffolds", *Journal of Biomedical Materials Research Part A* 67A(4):1105-1114, (Dec. 15, 2003), (Abstract only).

Li et al., "Electrospinning nanofibers as uniaxially aligned arrays and layer-by-layer stacked films", *Advanced Materials* 16(4):361-366, (2004), (Abstract only).

Li et al. "Multilineage differentiation of human mesenchymal stem cells in a three-dimensional nanofibrous scaffold", *Biomaterials* 26(25):5158-5166, (2005), (Abstract only).

Liang et M. "Developing gossypol derivatives with enhanced anti-tumor activity", *Investigational New Drugs* 13(3):181-186, (1995), (Abstract only).

Lieblein et al., "STAT3 can be activated through paracrine signaling in breast epithelial cells", *BMC Cancer*, 8(302):1-14, (2008).

Liu et at, "Function analysis of estrogenically regulated protein tyrosine phosphatase gamma (PTPgamma) in human breast cancer cell line MCF-7", *Oncogene*, 23(6):1256-1262, (2004).

Liu et al., "Involvement of breast epithelial-stromal interactions in the regulation of protein tyrosine phosphatase-gamma (PTPgamma) mRNA expression by estrogenically active agents", *Breast Cancer Research and Treatment*, 71(1):21-35, (2002).

Liu et al., "Transformation of MCF-10A Human Breast Epithelial Cells by Zeranol and Estradio1-17beta" (Nov.-Dec. 2004) *Breast J.* 10(6):514-521 (Abstract only).

Lo et al., "Cell movement is guided by the rigidity of the substrate", *Biophysical Journal*, 79(1):144-152, (200).

Luu et al., "Development of a nanostructured DNA delivery scaffold via electrospinning of PLGA and PLGA and PLA-PEG block copolymers", *Journal of Controlled Release* 89(2):341-353, (Apr. 29, 2003), (Abstract only).

Macchiarini et al., "Clinical Transplantation of a Tissue-Engineered Airway", *The Lancet* 372(9655):2023-2030, (Dec. 13, 2008), (Abstract only).

Martins et al., "Electrospun nanostructed scaffolds for tissue engineering applications", *Nanomedical*, 2(6):929-942, (2007).

Mathews, "Preparation and anisotropic mechanical behavior of highly-oriented elecrtospun poly(butylene terephthalate) fibers", *Journal of Applied Polymer Science*, 101(3):2017-2021, (2006).

Mcclure et al., "A Three-layered electrospun matrix to mimic native arterial architecture using polycaprolactone, elastin, and collagen: a preliminary study", *Acta Biomaterialia* 6:2422-2433, (2010).

Morawski et al., "Perineuronal nets potentially protect against oxidative stress", *Exp. Neurol.* 188(2):309-315, (2004), (Abstract only).

Morgenstern et al., "Chondroitin sulphate proteoglycans in the CNS injury response", *Prog. Brain Res.* 137:313-332, (2002), (Abstract only).

Mori et al., "Fibrocytes contribute to the myofibroblast population in wounded skin and originate from the bone marrow", *Experimental Cell Research* 304(1):81-90, (Mar. 10, 2005), (Abstract only).

Murray et al., "Hyper-responsiveness of IPF/UIP fibroblasts: Interplay between TGF β1, IL-13 and CCL2", 40(10):2174-2182, (2008), (Abstract only).

Nam et al. "Improved Cellular Infiltration in Electrospun Fiber via Engineered Porosity", *Tissue Engineering* 13(9):2249-2257, (2007), (Abstract only).

Nam et al. "Materials selection and residual solvent retention in biodegradable electrospun fibers", *Journal of Applied Polymer Science* 107(3):1547-1524, (Feb. 5, 2008), (Abstract only).

Nam et al., "Novel electrospun scaffolds for the molecular analysis of chondrocytes under dynamic compression", *Tissue Engineering: Part A* 15(3):513-523, (2009).

Nam et al. "Modulation of Embryonic Mesenchymal Progenitor Cell Differentiation via Control Over Pure Mechanical Modulus in Electrospun Nanofibers", *Acta Biomaterialia* 7(4):1516-1524, (2001), (Abstract only).

Ninomiya et al., "Transforming Growth Factor-β Signaling Enhances Transdifferentiation of Macrophages into Smooth Muscle-Like Cells", *Hypertension Research*, 29(4):269-276, (2006).

Norton et al. "Myelination in rat brain: method of myelin isolation", *J. Neurochem.* 21(4):749-757, (1973), (Abstract only).

Novak et al. "Extracellular matrix and the brain: components and function", *J. Clin. Neurosci.* 7(4):280-290, (2000), (Abstract only).

Ohnishi et al., "A Novel Model of Glioma Cell Invasion Using Organotypic Brain Slice Culture", *Cancer Research*, 58:2935-2940, (Jul. 15, 1998).

Palfi et al., "Correlation of in vitro infiltration with glioma histological type in organotypic brain slices", *Br. J. Cancer* 91(4):745-752, (2004).

Pelham et al., "Cell locomotion and focal adhesions are regulated by substrate flexibility", *PNAS USA* 94:13661-13665, (1997).

Pilkington "The paradox of neoplastic glial cell invasion of the brain and apparent metastatic failure", *Anticancer Res.* 17(6B):4103-4105, (1997), (Abstract only).

Powell et al., "EDC cross-linking improves skin substitute strength and stability", *Biomaterials* 27(34): 5821-5827, (2006), (Abstract only).

Properzi et al., "Proteoglycans and Brain Repair", News Physiol. Sci., 19:33-38, (2004).

Quigley et al., "The relationship between survival and the extent of the resection in patients with supratentorial malignant gliomas", *Neurosurgery* 29:385-389 (1999), (Abstract only).

Rao "Molecular mechanisms of glioma invasiveness: the role of proteases", *Nature Reviews Cancer* 3:489-501, (2003), (Abstract only).

Rath et al., "Compressive Forces Induce Osteogenic Gene Expression in Calvarial Osteoblasts", *Journal of Biomechanics* 41(5):1095-1103, (2008), (Abstract only).

Rauch "Extracellular matrix components associated with remodeling processes in brain", *Cell Mol. Life Sci.* 61:203102045, (2004).

Reneker et al., "Nanometre diameter fibres of polymer, produced by electrospinning", *Nanotechnology* 7(3):216-223, (1996), (Abstract only).

Rocks et al., "ADAMTS-1 Metalloproteinase Promotes Tumor Development through the Induction of a Stromal Reaction In vivo", *Cancer Research* 68(22):9541-9550, (2008).

Ruoslahti "Brain extracellular matrix" *Glycobiologhy* 6(5):489-492, (1996).

Sasmono et al., "A macrophage colony-stimulating factor receptor—green fluorescent protein transgene is expressed throughout the mononuclear phagocyte system of the mouse", *Blood* 101(3):1155-1163, (2003).

Saunders et al., "Fibrocyte localization to the airway smooth muscle is a feature of asthma", *Journal of Allergy and Clinical Immunology* 123(2): 376-384, (2009), (Abstract only).

Schmidt et al., "Identification of Circulating Fibrocytes as Precursors of Bronchial Myofibroblasts in Asthma", *Journal of Immunology* 171(1):380-389, (2003).

Shin et al., "Contractile cardiac grafts using a novel nanofibrous mesh", *Biomaterials* 25(17):3717-3723, (2004), (Abstract only).

Shin et al., "In Vivo Bone Tissue Engineering Using Mesenchymal Stem Cells on a Novel Electrospun Nanofibrous Scaffold", *Tissue Engineering* 10(1-2):33-41, (Jul. 9, 2004), (Abstract only).

Sieben et al., "PCR artifacts in LOH and MSI analysis of microdissected tumor cells", *Human Pathology* 31(11):1414-1419, (2000), (Abstract only).

Silver et al., "Regeneration beyond the glial scar", *Nature* 5:146-156, (2004).

(56) References Cited

OTHER PUBLICATIONS

Srikar et al., "Desorption-limited mechanism of release from polymer nanofibers", Langmuir 24(3):965-974, (2008).
Stein et al., "Estimating the cell density and invasive radius of three-dimensional glioblastoma tumor spheroids grown in vitro", *Applied Optics* 46(22):5110-5118, (Aug. 1, 2007).
Stitzel et al., "Controlled Fabrication of a Biological Vascular Substitute", *Biomaterials* 27:1088-1094, (2006).
Subramanian et al., "Metastasis to and from the central nervous system—the relatively protected site", *The Lancet Oncology* 3(8):498-507, (2002), (Abstract only).
Swanson et al. "A quantitative model for differential motility of gliomas in grey and white matter", *Cell Proliferation* 33(5):317-329. (2000), (Abstract only).
Swanson "Quantifying glioma cell growth and invasion in vitro", *Mathematical and Computer Modeling* 47:638-648, (2008).
Teo et al., "A review on electrospinning design and nanofibre assemblies", *Nanotechnology* 17(14):R86-R106, (2006).
Teo et al., "Electrospun fibre bundle made of aligned nanofibers over two fixed points", *Nanotechnology* 16:1878, (1978), (Abstract only).
Tomlinson et al., "Loss of heterozygosity analysis: Practically and conceptually flawed?", *Genes Chromosomes & Cancer* 34:349-353, (2002).
Tonn et al., "Mechanisms of glioma cell invasion", *Acta Neurochir* Suppl 88: 163-167, (2003), (Abstract only).
Toole "Hyaluronan and its binding proteins, the hyaladherins", *Curr. Opin. Cell Biol.* 2:839-844, (1990), (Abstract only).
Tse et al., "Current Status of Pipeline Embolization Device in the Treatment of Intracranial Aneurysms: A review", *World Neurosurgery* 80(6): 829-835, (2013).
Tuszynski et al., "Differential cytotoxic effect of gossypol on human melanoma, colon carcinoma, and other tissue culture cell lines", *Cancer Research* 44(2):768-771, (1984).
Van Meter et al., "The role of matrix metalloproteinase genes in glioma invasion: co-dependent and interactive proteolysis", *Journal of Neuro-Oncology* 53:213-235, (2001).
Viapiano et al., "BEHAB/brevican requires ADAMTS-mediated proteolytic cleavage to promote glioma invastion", *J. Neurooncol.* 88:261-272, (2008).
Viapiano et al. "From barriers to bridges: chondroitin sulfate proteoglycans in neuropathology", *Trends Mol. Med.* 12(10):488-496, (2006), (Abstract only).
Vuorinen et al., "Debulking or biopsy of malignant glioma in elderly people—a andomized study", *Trends Mol. Med.* 12(10):488-496, (2006).
Wang et al., "Conjugated Linoleic Acid (CLA) Up-regulates the Estrogen-regulated Cancer Suppressor Gene, Protein Tyrosine Phosphatase gamma (PTPgamma), in Human Breast Cells", *Anticancer Research* 26(1A):27-34, (2006).
Wang et al., "Effect of gossypol on DNA synthesis and cell cycle progression of mammalian cells in vitro", Cancer Research 44(1):35-38, (1984).
Wang et al., "Nanofibres and their influence on Cells for Tissue Regeneration", *Aust. J. Chem.* 58(10):704-712,(2005).
Wang et al., "Increased Circulating Fibrocytes in Asthma with Chronic Airflow Obstruction", *Am. J. Respir. Crit. Care Med.* 178(6):583-591, (2008).
Williams et al. "Anti-glioma effects of protein kinase inhibitors that simultaneously block invasion and proliferation" (Oct. 2007) Abstracts from 12th Annual Meeting of the Society for Neuro-Oncology 9: 486 ET-18 (Abstract only).
Wu et al. "Versican protects cells from oxidative stress-induced apoptosis" (Feb. 2005) *Matrix Biology* 24(1):3-13 (Abstract only).
Wu et al., "An in vitro and in vivo study of antitumor effects of gossypol on human SW-13 adrenocortical carcinoma", *Cancer Research* 49(14):3754-3758, (1986).
Wykosky et al., "Soluble monomeric EphrinA1 is released from tumor cells and is a functional ligand for the EphA2 receptor", *Oncogene* 27(58):7260-7273, (2008).

Xie et al., "Encapsulation of protein drugs in biodegradable microparticles by co-axial electrospray", *Journal of Colloid and Interface Science* 317(2):469-476, (Jan. 15, 2008).
Xie et al., "White matter inhibitors in CNS axon regeneration failure", *Exp. Neurol.* 209(2):302-312, (2007), (Abstract only).
Yamaguchi "Lecticans: organizers of the brain extracellular matrix" *Cell Mol. Life Sci.* 57:276-289, (2000).
Yang et al., "Integrin $\alpha 1\beta 1$ and $\alpha 2\beta 1$ are the key regulators of hepatocarcinoma cell invasion across the fibrotic matrix microenvironment", Cancer Research 63(23):8312-8317, (Dec. 1, 2013).
Yoo et al., "Surface-Functionalized Electrospun Nanofibers for Tissue Engineering and Drug Delivery", Advanced Drug Delivery Reviews 61:1033-1042, (Jan. 1, 2009).
Yoshimoto et al., "A biodegradable nanofiber scaffold by electrospinning and its potential for bone tissue engineering", *Biomaterials* 24(12):2077-2082, (2003), (Abstract only).
Yu et al., "Production of submicrometer diameter fibers by two-fluid electrospinning", *Adv. Mater.* 16(17):1562-1566, (2004), (Abstract only).
Zborowski et al., "Red blood cell magnetophoresis", *Biophysical Journal* 84:2638-2645, (2003).
Zeng et al. "Enzymatic degradation of poly(L-lactide) and poly($\varepsilon$-caprolactone) electrospun fibers", *Macromolecular Bioscience* 4(12):1118-1125, (Dec. 15, 2004). (Abstract only).
Zeng et al. "Ultrafine fibers electrospun from biodegradable polymers", *Journal of Applied Polymer Science* 89(4):1085-1092, (Jul. 25, 2003), (Abstract only).
Zhang et al., "Electrospinning of gelatin fibers and gelatin/PCL composite fibrous scaffolds", *J. Biomed. Mater. Res. Part B: Appl. Biomater.* 72B(1):156-165, (2005).
Zhang et al., "Recent development of polymer nanofibers for biomedical and biotechnological applications", *Journal of Materials Science—Materials in Medicine* 16(10):933-946, (2005).
International Search Report and Written Opinion for PCT/US2016/030058 dated Jul. 29, 2016.
Chen et al., Preparation and Characterization of Coaxial Electrospun Thermoplastic Polyurethane/Collagen Compound Nanofibers for Tissue Engineering Applications, *Colloids and Surfaces B-Biointerfaces* (2010), 79(2):315-325.
Pham et al., Electrospinning of Polymeric Nanofibers for Tissue Engineering Applications: A Review, Tissue Engineering (2006), 12(5):1197-1211.
Frey et al. "Electrospinning and Porosity Measurements of Nylon6 PEO blended Nonwovens" Journal of Engineered Fibers and Fabrics (2007), 2(1):31-37.
Hashi et al. "Antithrombogenic Modification of Small Diameter Microfibrous Vascular Grafts" Arterioscler Thromb Vasc Biol. (Aug. 2010), 30(8):1621-1627.
Meng et al., Journal of Nanoscience and Nanotecimology (Jul. 8, 2010), 312-320.
Ayres et al., "Microvascular Endothelial Cell Migration in Scaffolds of Electrospun Collagen," Wound Repair and Regeneration (Mar. 2005), 13(2):A6 (abstract only).
Park, Lab-made organ implanted for first time (Jul. 14, 2017), CNN.com, <http://www.cnn.com/2011/HEALTH/07/07/trachea.transplant/index.html>.
International Search Report and Written Opinion for International Application No. PCT/US2016/060157 dated Jan. 31, 2017.
Lee et al., "Biomedical Applications of Magnetically Functionalized Organic/Inorganic Hybrid Nanofibers," International Journal of Molecular Sciences (Jun. 15, 2015), 16 pp. 13661-13677.
Samios et al., "In situ compatibilization of polyurethane with poly(ethylene terephthalate)," Department of Chemistry, European Polymer Journal (2000), 36 pp. 937-947.
Supplemental European Search Report and Written Opinion for EP15774154 dated Sep. 22, 2017.
Barnhart et al. "Evaluation of an intra-articular synthetic ligament for treatment of cranial cruciate ligament disease in dogs: a six-month prospective clinical trial" Jun. 2016, Vet Comp Orthop. Traumatol. 29:491-498.
Albertini et al. "The effect of glycosaminoglycans and proteoglycans on lipid peroxidation" (Aug. 2000) Int. J. Mol. Med. 6(2):129-136 (Abstract only).

(56) References Cited

OTHER PUBLICATIONS

Brown et al., "Synthesis, X-ray Opacity, and Biological Compatibility of Ultra-High Payload Elemental Bismuth Nanoparticle X-ray Contrast Agents" Chemistry of Materials (Mar. 10, 2014), (26) pp. 2266-2274.
Bull et al., "Self-Assembled Peptide Amphiphile Nanofibers Conjugated to MRI Contrast Agents", American Chemical Society (Jan. 2005), 5(1) pp. 1-4.
Chalmers et al. "Chapter 9. Preparative applications of magnetic separation in biology and medicine" (2007) Laboratory Techniques in Biochemistry and Molecular Biology 32:249-264 (Abstract only).
Delpech et al. "Hyaluronan and hyaluronectin in the nervous system" (Sep. 28, 2007) Ciba Foundation Symposium 143—The Biology of Hyaluronan (Abstract only).
Liu et al. The (-)-enantiomer of gossypol possesses higher anticancer potency than racemic gossypol in human breast cancer: (2002) Anticancer Research 22(1A):33-38 (Abstract only).
Lotfi et al., "Resilon: A Comprehensive Literature Review", Journal of Dental Research, Dental Clinics, Dental Prospects (2013), 7(3) pp. 119-131.
Thomas et al. "Effects of gossypol on the cell cycle phases in T-47D human breast cancer cells" (Jul.-Aug. 1991) Anticancer Research 11(4):1469-1476 (Abstract only).
Zilla and Human, Prosthetic vascular grafts: Wrong models, wrong questions and no healing. Biomaterials, 2007. 28(34): p. 5009-5027.
Baker et al. "The Potential to Improve Cell Infiltration in Composite Fiber-Aligned Electrospun Scaffolds by the Selective Removal of Sacrificial Fibers", Biomaterials, May 2008, pp. 2348-2358, vol. 29, No. 15.

\* cited by examiner

FIBER SCAFFOLDS FOR USE IN ESOPHAGEAL PROSTHESES

CROSS-REFERENCE TO RELATED APPLICATIONS

This application is a continuation of U.S. patent application Ser. No. 13/385,612, filed Feb. 9, 2012, entitled "Fiber Scaffolds for Use in Esophageal Prostheses," which claims priority to and benefit of U.S. Provisional Patent Application No. 61/466,039, filed Mar. 22, 2011, entitled "Electrospinning for Highly Aligned Nanofibers," U.S. Provisional Patent Application No. 61/562,090, filed Nov. 21, 2011, entitled "Nanofiber Scaffolds for Biological Structures," and U.S. Provisional Patent Application No. 61/585,869, filed Jan. 12, 2012, entitled "Biocompatible Nanofiber Materials for Biological Structures," the entire contents of each of which is incorporated herein by reference.

BACKGROUND OF THE INVENTION

The esophagus is an organ within the neck that permits travel of food and saliva from the mouth to the stomach through peristalsis. It has a generally tubular shape consisting of multiple layers ranging from a mucosa layer on the lumen consisting primarily of epithelial cells to a muscular adventitia consisting primarily of smooth muscle cells, striated muscle cells and fibroblasts. The inner layer of muscle is oriented in a circumferential direction while the outer layer of muscle is oriented in a longitudinal direction (see FIG. 1). When at rest, the esophagus is nearly collapsed, but can expand to roughly 3 cm in diameter upon swallowing.

Peristalsis involves involuntary movements of the longitudinal and circular muscles, primarily in the digestive tract but occasionally in other hollow tubes of the body, that occur in progressive wavelike contractions. Peristaltic waves occur in the esophagus, stomach, and intestines. The waves can be short, local reflexes or long, continuous contractions that travel the whole length of the organ, depending upon their location and what initiates their action. In the esophagus, peristaltic waves begin at the upper portion of the tube and travel the whole length, pushing food ahead of the wave into the stomach. Particles of food left behind in the esophagus initiate secondary peristaltic waves that remove leftover substances. One wave travels the full length of the tube in about nine seconds. Peristaltic waves start as weak contractions at the beginning of the stomach and progressively become stronger as they near the distal stomach regions. The waves help to mix the stomach contents and propel food to the small intestine. Usually, two to three waves are present at one time in different regions of the stomach, and about three waves occur each minute.

In the large intestine (or colon), the peristaltic wave, or mass movement, is continuous and progressive; it advances steadily toward the anal end of the tract, pushing waste material in front of the wave. When these movements are vigorous enough to pass fecal masses into the rectum, they are followed by the desire to defecate. If feces are passed to the rectum and not evacuated from the body, they are returned to the last segment of the colon for longer storage by reverse peristaltic waves. Peristaltic waves are particularly important in helping to remove gas from the large intestine and in controlling bacterial growth by mechanically acting as a cleansing agent that dislodges and removes potential colonies of bacteria.

Partial loss or complete loss of peristalsis due to the loss of the esophagus, small intestine and/or large intestine due to cancer or other diseases can have a catastrophic, if not fatal, effect on an animal. A number of in vivo prostheses for luminal structures such as the esophagus are known. Typically these prostheses are formed by donor structures from cadavers or are manmade structures. However, these existing structures are subject to failure due to anastomotic stenosis, luminal stenosis, infection, dislocation, and migration, among other causes. Therefore, there is an ongoing need for artificial or prosthetic versions of organs such as the esophagus and intestinal tract that will provide the patient, human or otherwise, with a functioning replacement for the lost organ.

DESCRIPTION OF THE DRAWINGS

The file of this patent contains at least one photograph or drawing executed in color. Copies of this patent with color drawing(s) or photograph(s) will be provided to the Patent and Trademark Office upon request and payment of necessary fee.

The accompanying drawings, which are incorporated into and form a part of the specification, schematically illustrate one or more exemplary embodiments of the invention and, together with the general description given above and detailed description given below, serve to explain the principles of the invention, and wherein.

DESCRIPTION OF THE INVENTION

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

Figure 1A:
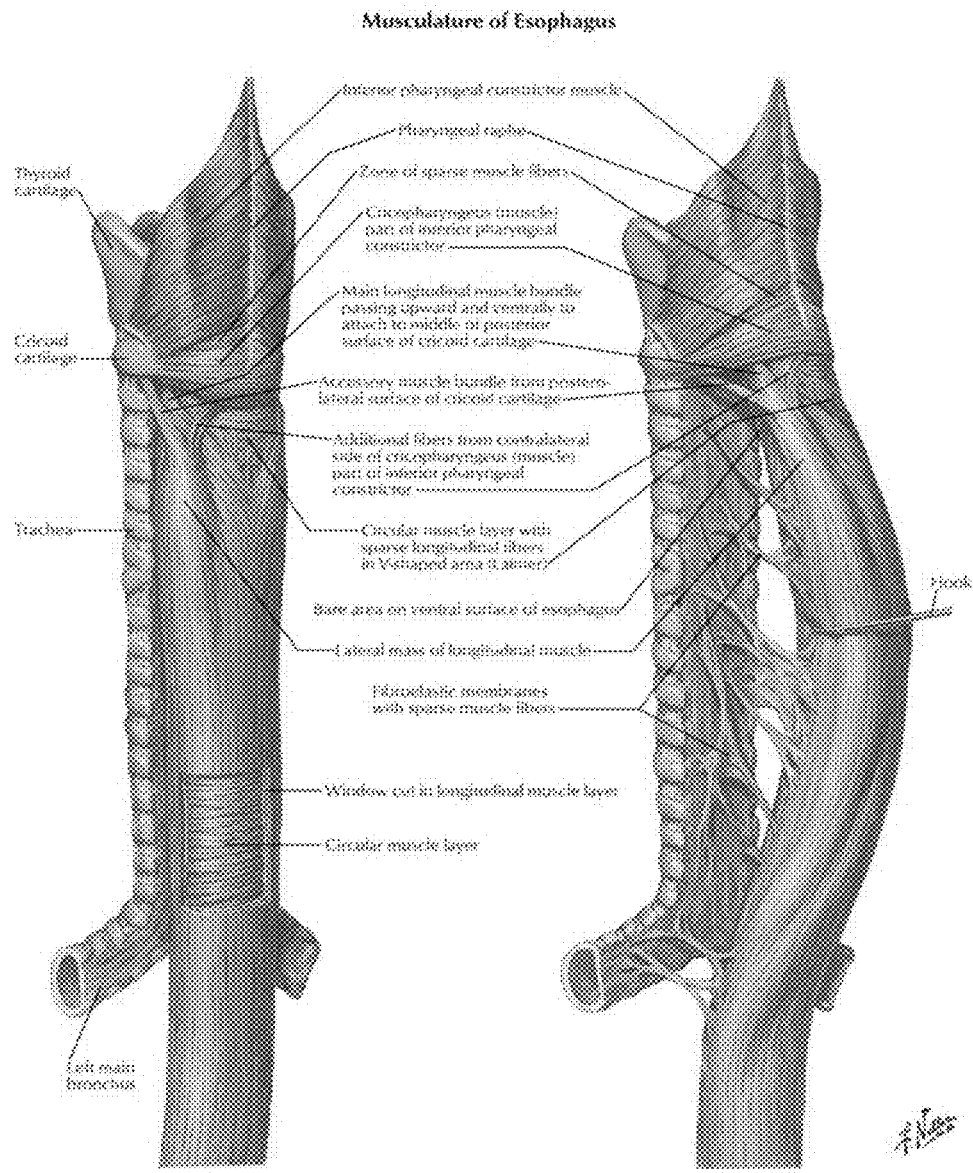
FIG. 1A is an illustration of the anatomy of the esophagus from Frank H. Netter
Figure 1B:
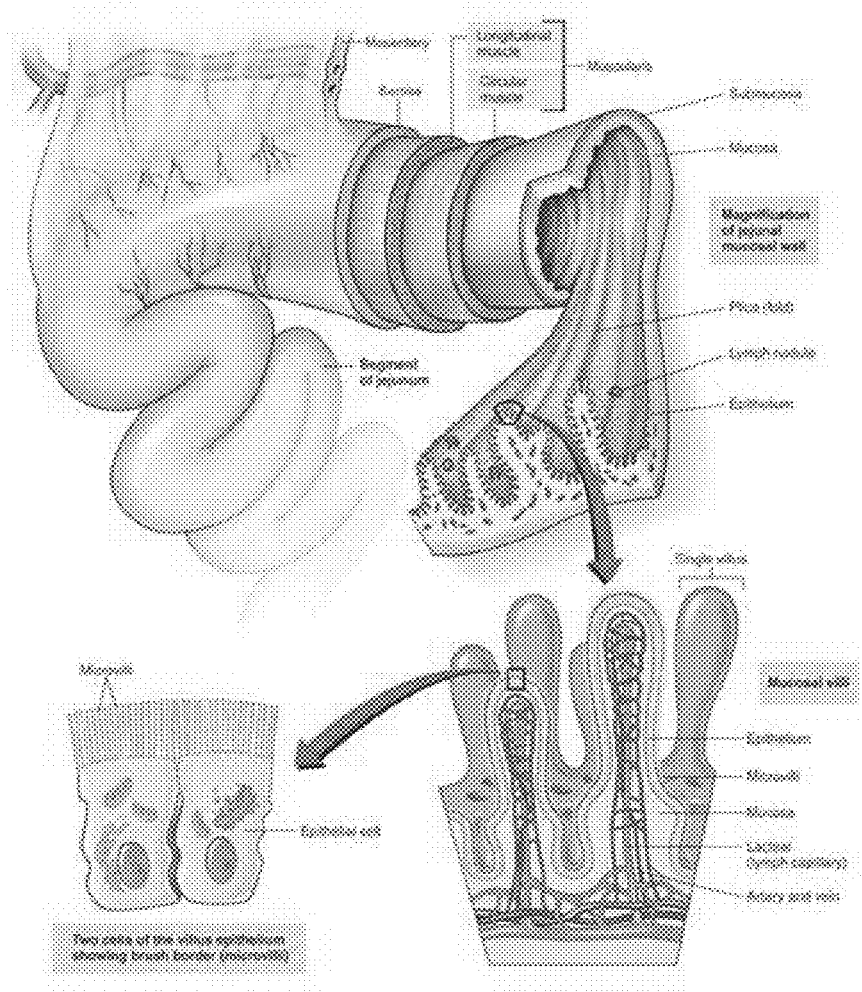
FIG. 1B is an illustration of a portion of the small intestine.
Figure 6:
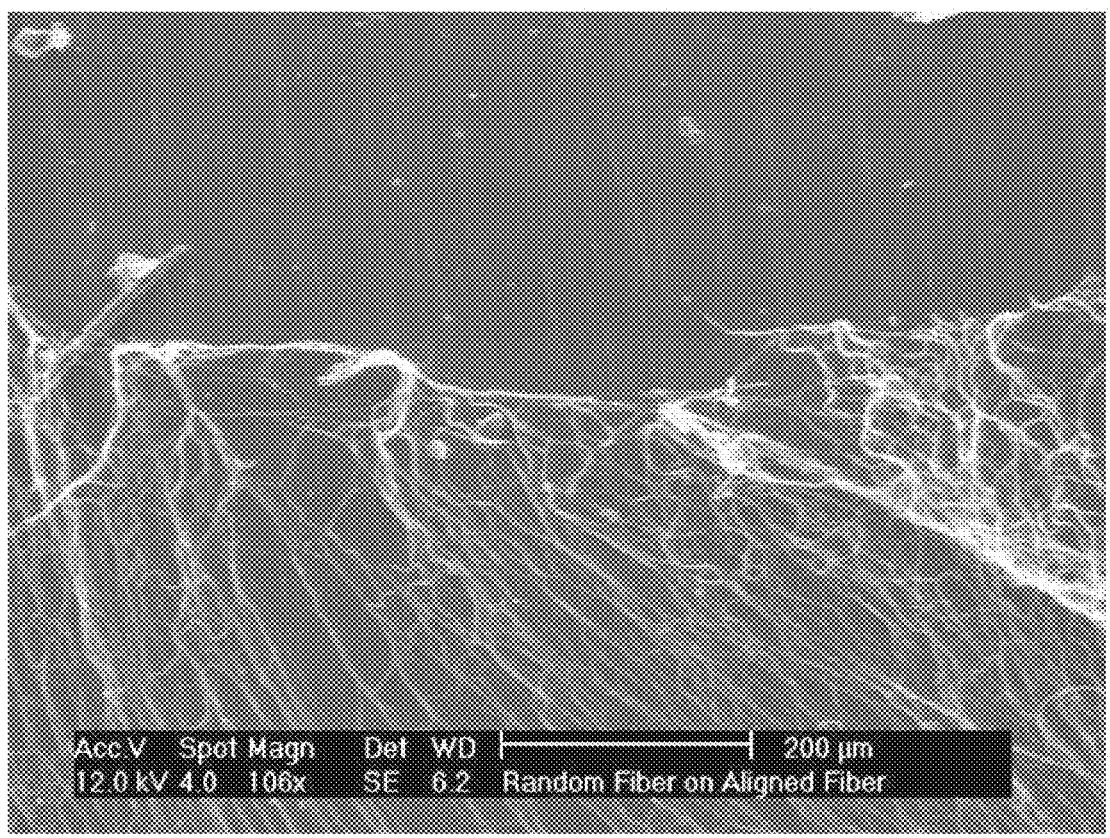
FIG. 6 is an SEM image of composite fiber scaffold that includes both oriented fibers and random fibers.

The present invention relates generally to the development and construction of implantable artificial organs, and more specifically to a process for manufacturing three-dimensional polymer microscale and nanoscale structures for use as scaffolds in the growth of biological structures such as hollow organs, luminal structures, or other structures within the body, particularly the esophagus (see FIG. 1A) and/or the small intestine, large intestine, duodenum, and jejunum. Exemplary versions of the manufacturing process of this invention include preparing a preform that is based on an actual organ; electro spinning one or more layers of nanoscale (less than 1000 nanometers) or microscale (less than 50 microns) polymer fibers on the preform to form a nanofiber based scaffold. The fibers are typically formed by electrospinning by extruding a polymer solution from a fiberization tip; creating an electronic field proximate to the fiberization tip; and positioning a ground or opposite polarity within the preform. The preform may be rotated to align the fibers on the preform or a second ground or polarity may be placed in the preform and rapidly switching the electric field to align the fibers. The microscale and nanoscale polymer fibers may be randomly aligned or maybe substantially parallel or both (see FIG. 6). These nanofiber structures may be seeded with one or more types of biological cells prior to implantation in the body to increase the rate of tissue growth into the scaffold. The scaffold may include autologous or allogenic cells such as cord blood cells, embryonic stem cells, induced pluripotent cells, mesenchymal cells, placental cells, bone marrow derived cells, hematopoietic cell, epithelial cells, endothelial cells, fibroblasts, chondrocytes or combinations thereof.

Figure 2:
FIG. 2 is a photograph of an exemplary fiber deposition system, in accordance with the present invention.
Figures 3A, 3B, 3C, 3D:
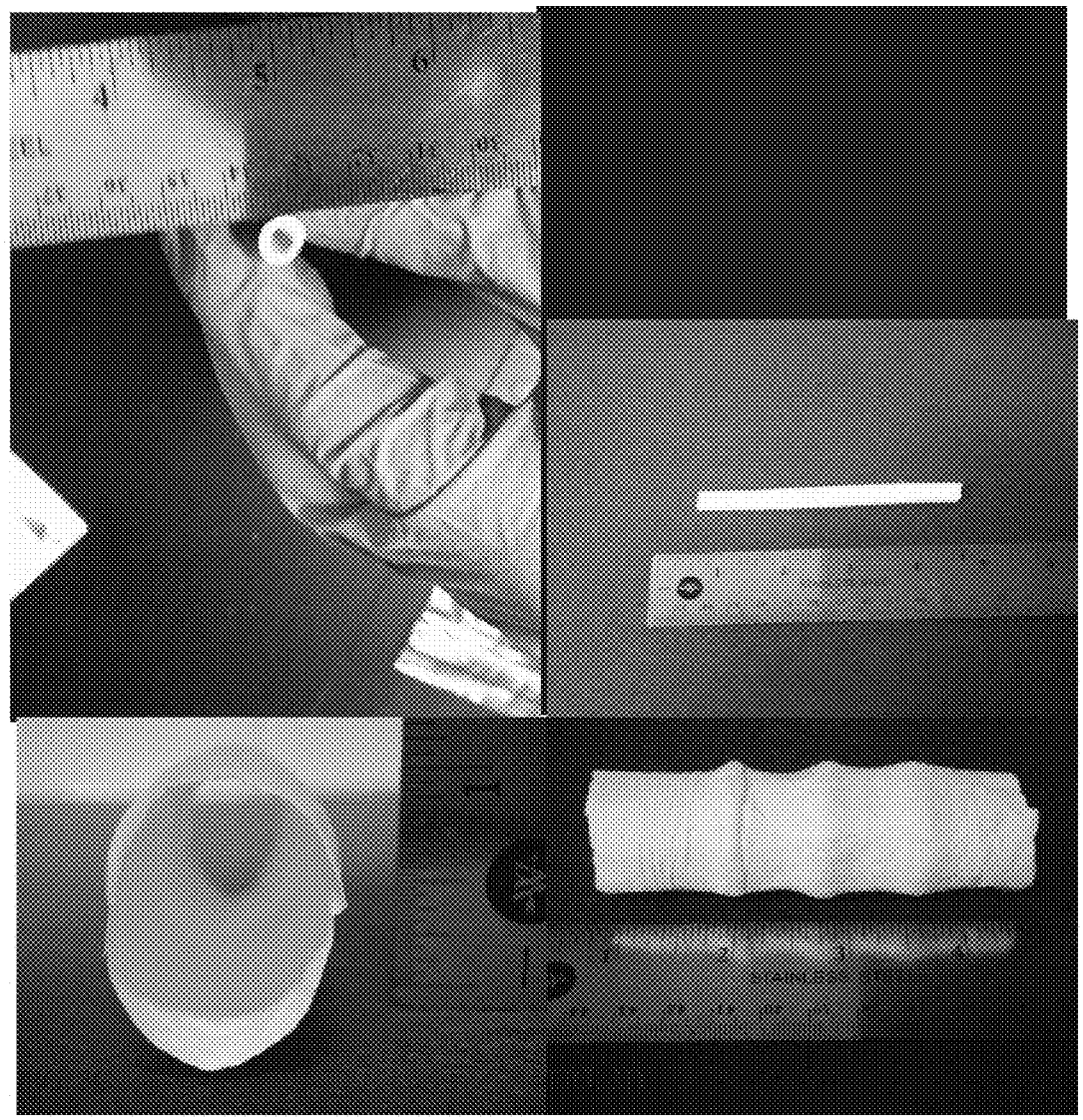
FIGS. 3A, 3B, 3C and 3D provide several photographs of examples of relatively small and large diameter tubes and irregular shapes derived from electrospun fiber made with the process of the present invention.
Figure 4A:
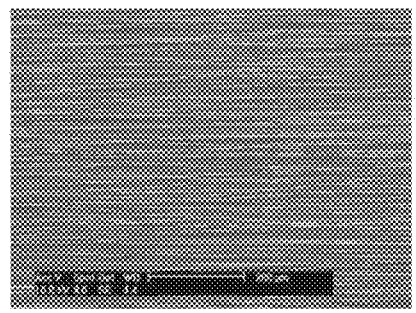
FIGS. 4A, 4B, 4C and 4D provide a number of photographs illustrating the control of cell orientation and differentiation based on discrete fiber alignment.
Figure 4B:
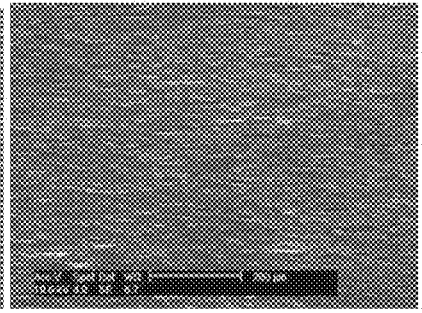
Figure 4C:
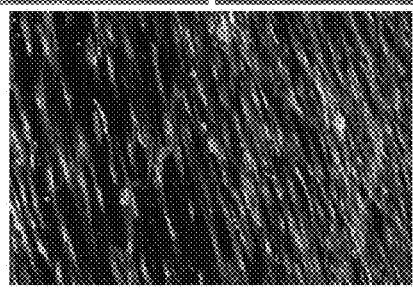
Figure 4D:
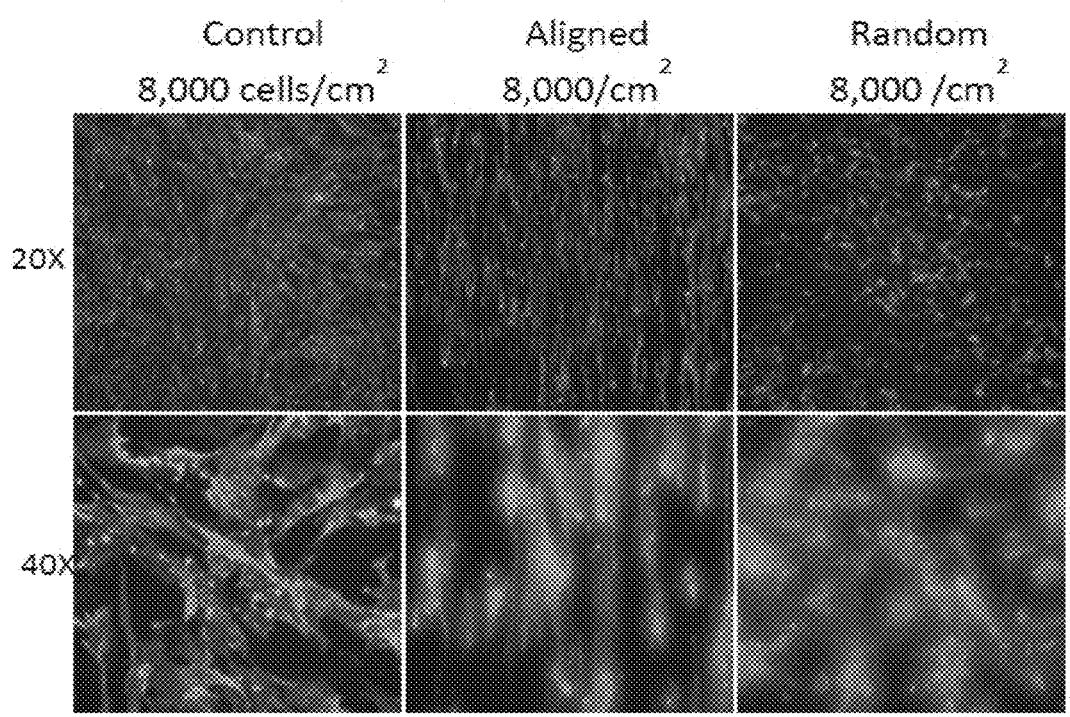

Choosing a material that accurately mimics the mechanical properties of the native esophagus (or other organ) can promote proper stem cell differentiation and facilitate normal esophageal function such as peristalsis. Materials may be non-resorbable for permanent implantation or may be designed to slowly degrade while the host body rebuilds the native tissue until the implanted prosthesis is completely resorbed. Permanent polymers may include polyurethane, polycarbonate, polyester terephthalate and degradable materials may include polycaprolactone, polylactic acid, polyglycolic acid, gelatin, collagen, or fibronectin. The fibers may be electrospun onto a preform with the desired prosthesis shape (see FIG. 2). FIG. 2 is a photograph of an exemplary setup of a 5 mm diameter rod with electrospun fiber being deposited onto the surface. The exemplary mandrel is coated with Teflon to facilitate removal of the scaffold after deposition or a slight taper (≈1°) can be manufactured into the mandrel. Nearly any size or shape can be produced from the electrospun fibers by using a pre-shaped form and deposition method as shown in FIGS. 3A-3D.

Figures 5A, 5B:
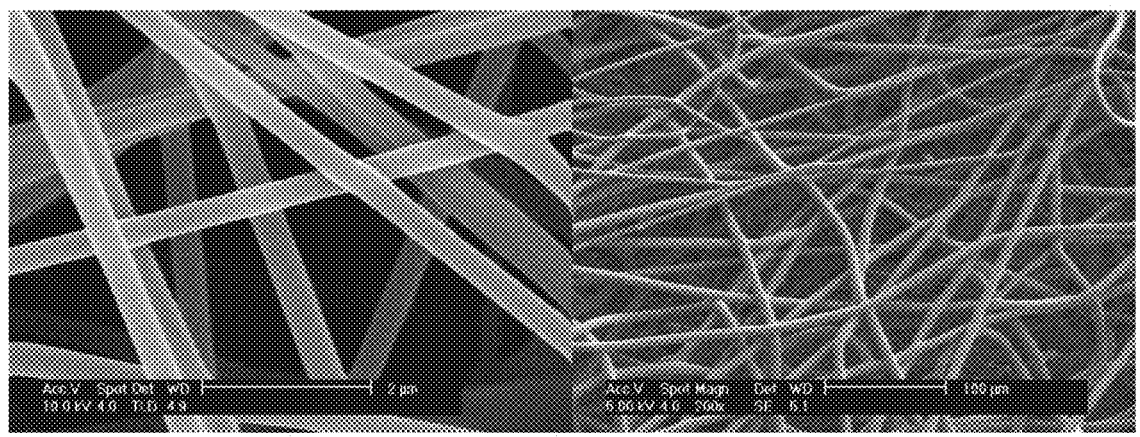
FIGS. 5A and 5B provide photographs of a 200 nm diameter fiber (on the left) with pore sizes of a few microns and a 20 um diameter fiber (on the right) with pore sizes of around 50 um.

Closely mimicking the structural aspects of the native esophagus (or other organ) is important with regard to replicating the function of the native esophagus. By controlling the orientation of the fibers and assembling a composite structure of different materials and/or different fiber orientations it is possible to control and direct cell orientation and differentiation (see FIGS. 4A-4D). Fiber orientation can be altered in each layer of a composite or sandwich scaffold in addition to the material and porosity to most closely mimic the native tissue. A properly constructed scaffold will permit substantially complete cellular penetration and uniform seeding for proper function and prevention of necrotic areas developing. If the fiber packing is too dense, then cells may not be able to penetrate or migrate from the exposed surfaces into the inner portions of the scaffold. However, if the fiber packing is not close enough, then the attached cells may not be able to properly fill the voids, communicate and signal each other and a complete tissue or organ may not be developed. Controlling fiber diameter can be used to change scaffold porosity as the porosity scales with fiber diameter (see FIGS. 5A-5B). Alternatively, blends of different polymers may be electrospun together and one polymer preferentially dissolved to increase scaffold porosity. The properties of the fibers can be controlled to optimize the fiber diameter, the fiber spacing or porosity, the morphology of each fiber such as the porosity of the fibers or the aspect ratio, varying the shape from round to ribbon-like. The precursor solution described below may be controlled to optimize the modulus or other mechanical properties of each fiber, the fiber composition, the degradation rate (from rapidly biosoluable to biopersitent. The fibers may also be formed as drug eluting fibers, anti-bacterial fibers or the fibers may be conductive fibers, radio opaque fibers to aid in positioning or locating the fibers in an x-ray, CT or other scan.

The effects of mechanical strain on electrospun polymer scaffolds has been described in the literature (see, *Microstructure-Property Relationships in a Tissue Engineering Scaffold*, Johnson et al., Journal of Applied Polymer Science, Vol. 104, 2919-2927 (2007) and *Quantitative Analysis of Complex Glioma Cell Migration on Electrospun Polycaprolcatone Using Time-Lapse Microscopy*, Johnson et al., Tissue Engineering; Part C, Volume 15, Number 4, 531-540 (2009), which are incorporated by reference herein, in their entirety, for all purposes). Strains as low as 10% appear to rearrange and align the fibers in the direction of loading. This alignment increases with the applied strain until over 60% of the fibers are aligned within ±10% of the direction of applied stress. If cells are present during fiber rearrangement in vivo or in vitro, they could conceivably be affected by these changes depending on the overall rate of strain. Fiber alignment is retained following a single cycle of extension and release. This has significant biological implications for a broad array of future tissue-engineering operations. As cells move across such a substrate, biased motion is likely as locomotion is based on forming and then dissolving a series of focal adhesions. Formation of these adhesions along the fiber direction may be easier than those perpendicular to that direction although this will be partially controlled by the spacing between the fibers. This has longer-term consequences for the eventual control of the architecture of tissues that develop upon such substrates.

Cellular mobility parallel to the fiber direction means that one could conceivably control and direct cell proliferation and migration by prestraining scaffolds to align the fibers in certain directions. This could result in tailored structures with highly aligned fibers and, as a result, highly aligned cells. Of additional importance is the fact that many envisioned applications of tissue-engineering scaffolds will involve the use of cyclic stresses designed to achieve specific architectures in the biological component of the developing tissue. If the scaffold experiences continuing hysteresis in which orientation increases versus the number of cycles the efficiency of the overall process will be greatly enhanced. For blood vessels, as an example, the application of cyclic pressures will produce preferential stresses that could cause significant alignment of the fibers in the circumferential direction. This could cause cellular alignment in the circumferential direction, potentially creating a more biomimetic arrangement.

Within the context of this invention, electrospinning is driven by the application of a high voltage, typically between 0 and 30 kV, to a droplet of a polymer solution or melt at a flow rate between 0 and 50 ml/h to create a condition of charge separation between two electrodes and within the polymer solution to produce a polymer jet. A typical polymer solution would consist of a polymer such as polycaprolactone, polystyrene, or polyethersulfone and a solvent such as 1,1,1,3,3,3-Hexafluoro-2-propanol, N,N-Dimethylformamide, Acetone, or Tetrahydrofuran in a concentration range of 1-50 wt %. As the jet of polymer solution travels toward the electrode it is elongated into small diameter fibers typically in the range of 0.1-30 µm.

In preparing an exemplary scaffold, a polymer nanofiber precursor solution is prepared by dissolving 2-30 wt % polyethylene terephthalate (PET) (Indorama Ventures) in a mixture of 1,1,1,3,3,3-hexafluoroisopropanol and trifluoroacetic acid and the solution is heated to 60° C. followed by continuous stirring to dissolve the PET. The solution may be cooled to room temperature and the solution placed in a syringe with a blunt tip needle. The nanofibers are formed by electrospinning using a high voltage DC power supply set to 1 kV-40 kV positive or negative polarity, a 5-30 cm tip-to-substrate distance, and a 1 µl/hr to 100 mL/hr flow rate. It is possible to use a needle array of up to 1,000's of needles to increase output. Approximately 0.2-3 mm thickness of randomly oriented and/or highly-aligned fibers may be deposited onto the form, and polymer rings added, followed by an additional approximately 0.2-3.0 mm of fiber added while the form is rotated. The scaffold may be placed in a vacuum overnight to ensure removal of residual solvent (typically less than 10 ppm) and treated using a radio frequency gas plasma for 1 minute to make the fibers more hydrophilic and promote cell attachment.

In accordance with this invention, an exemplary preparation of electrospinning solution typically includes of polyethylene terephthalate (PET), polycaprolactone (PCL), polylactic acid (PLA), polyglycolic acid (PGA), polyetherketoneketone (PEKK), polyurethane (PU), polycarbonate (PC), polyamide (Nylon), natural polymers such as fibronectin, collagen, gelatin, hyaluronic acid or combinations thereof that are mixed with a solvent and dissolved. A form is prepared for the deposition of nanofibers. Optionally, simulated cartilage or other supportive tissue may be applied to the form and the fibers are then sprayed onto or transferred onto a form to build up the scaffold. The present invention may be useful for the preparation of a number of bodily tissues, including hollow organs, three-dimensional structures within the body such as trachea, esophagus, intestine or luminal structures, such as nerves (epineurium or perineurium), veins and arteries (aorta, tunica externa, external elastic lamina, tunica medica, internal elastic lamina, tunica inima). Other preforms for mammals such as primates, cats, dogs, horses and cattle may be produced.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

For example, the present invention encompasses the following exemplary embodiments and variants thereof: (i) a composite scaffold seeded with stem cells and promoted to differentiate into stratified tissue; (ii) separate scaffold layers or sheets seeded independently to form different types of tissue and then assembled together using sutures, adhesive or welding to form a tubular shape and the stratified tissue; (iii) a scaffold implanted without cells for immediate replacement of damaged tissue and allow for cellular migration in vivo; (iv) an electrospun fiber scaffold made from non-resorbable materials such as polyethylene terephthalate, polyurethane, polycarbonate, poly ether ketone ketone; (v) an electrospun fiber scaffold made from resorbable materials such as polycaprolactone, polylactic acid, polyglycolic acid; (vi) an electrospun fiber scaffold made from natural polymers such as collagen, gelatin, fibronectin, hyaluronic acid or any combination of material types; (vii) an electrospun fiber scaffold made from a single layer of oriented fibers or a composite comprising layers of oriented fiber to correspond to the native structure and help orient and differentiate cells (fiber orientation can be from a rotating mandrel (circumferential fiber alignment), a translating mandrel (longitudinal fiber alignment), or split ground method of using electrostatics to align the fiber); (viii) using a pre-shaped mandrel or form to deposit fibers onto to achieve a near net shaped esophagus or intestine or other organs that support/perform peristalsis—the pre-shaped form can have a slight taper machined into the mandrel or coated with a non-stick surface to allow easy removal of the scaffold; and (ix) using a pre-shaped mandrel or form to deposit fibers onto to achieve a near net shaped esophagus segment/patch or intestine segment/patch or other organ segment/patch that supports/performs peristalsis. A pre-shaped form can have a slight taper machined into the mandrel or coated with a non-stick surface to allow easy removal of the scaffold.

The invention claimed is:

1. An implantable artificial organ scaffold comprising:
   one or more electrospun fibers, each fiber comprising a polymer and a radio opaque compound;
   wherein the one or more electrospun fibers are formed into a layer having a fiber orientation selected from the group consisting of substantially parallel, randomly oriented, and a combination thereof, wherein the layer has a fiber spacing from about 2 µm to about 50 µm; and
   wherein the implantable artificial organ scaffold is formed into a luminal structure having an interior surface that is smooth on the microscale.

2. The implantable artificial organ scaffold of claim 1, further comprising a plurality of biological cells seeded on the scaffold, the biological cells selected from the group consisting of cord blood cells, embryonic stem cells, induced pluripotent cells, mesenchymal cells, placental cells, bone marrow derived cells, hematopoietic cells, epithelial cells, endothelial cells, fibroblast cells, chondrocyte cells, and combinations thereof.

3. The implantable artificial organ scaffold of claim 1, wherein the luminal structure has a shape of a biological organ selected from the group consisting of an esophagus, a small intestine, a large intestine, a duodenum, and a jejunum.

4. The implantable artificial organ scaffold of claim 1, further comprising a supportive material.

5. The implantable artificial organ scaffold of claim 4, wherein the supportive material comprises simulated cartilage.

6. A method of fabricating an implantable artificial organ scaffold, the method comprising:
   depositing, by electrospinning, a layer of one or more fibers comprising a polymer and a radio opaque compound onto a preform, wherein the layer has a fiber orientation selected from the group consisting of substantially parallel, randomly oriented, and a combination thereof, wherein the layer has a fiber spacing from about 2 µm to about 50 µm and wherein the layer is formed into a luminal structure having an interior surface that is smooth on the microscale; and
   removing the layer from the preform.

7. The method of claim 6, wherein the preform has a shape based on a biological organ selected from the group consisting of an esophagus, a small intestine, a large intestine, a duodenum, and a jejunum.

8. The method of claim 6, further comprising seeding a plurality of biological cells onto the layer.

9. The method of claim 8, wherein the biological cells are selected from the group consisting of cord blood cells, embryonic stem cells, induced pluripotent cells, mesenchymal cells, placental cells, bone marrow derived cells, hematopoietic cells, epithelial cells, endothelial cells, fibroblast cells, chondrocyte cells, and combinations thereof.

10. The method of claim 6, further comprising subjecting the layer to a mechanical stress.

11. The method of claim 6, wherein the electrospinning comprises:
   extruding a polymer solution from a fiberization tip;
   creating an electronic field proximate to the fiberization tip; and
   providing a ground or opposite polarity to the preform.

12. The method of claim 11, wherein the polymer solution comprises a polymer and one or more radio opaque compounds.

13. The method of claim 11, wherein the polymer solution comprises a polymer and one or more of fluorescence compounds, anti-bacterial compounds, growth hormones, conductive compounds, ceramic compounds, and metallic compounds.

\* \* \* \* \*